(12) United States Patent
Bharat et al.

(10) Patent No.: US 11,596,386 B2
(45) Date of Patent: Mar. 7, 2023

(54) LARGE AREA ULTRASOUND TRANSDUCER ASSEMBLY AND SENSOR TRACKING FOR APERTURE CONTROL AND IMAGE GNERATION

(71) Applicant: KONINKLIJKE PHILIPS N.V., Eindhoven (NL)

(72) Inventors: Shyam Bharat, Arlington, MA (US); Man Nguyen, Melrose, MA (US); Ameet Kumar Jain, Boston, MA (US); Jean-Luc Francois-Marie Robert, Cambridge, MA (US); Vijay Parthasarathy, Lexington, MA (US); Atul Gupta, Bala Cynwyd, PA (US); Kunal Vaidya, Boston, MA (US); Ramon Quido Erkamp, Swampscott, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 648 days.

(21) Appl. No.: 16/479,303

(22) PCT Filed: Jan. 11, 2018

(86) PCT No.: PCT/EP2018/050601
§ 371 (c)(1),
(2) Date: Jul. 19, 2019

(87) PCT Pub. No.: WO2018/134106
PCT Pub. Date: Jul. 26, 2018

(65) Prior Publication Data
US 2019/0380679 A1    Dec. 19, 2019

Related U.S. Application Data

(60) Provisional application No. 62/448,067, filed on Jan. 19, 2017.

(51) Int. Cl.
*A61B 34/20*    (2016.01)
*A61B 8/00*    (2006.01)
*A61B 8/08*    (2006.01)

(52) U.S. Cl.
CPC .......... *A61B 8/4209* (2013.01); *A61B 8/0841* (2013.01); *A61B 8/0891* (2013.01);
(Continued)

(58) Field of Classification Search
CPC ... A61B 8/4209; A61B 8/0841; A61B 8/0891; A61B 8/4477; A61B 8/4494; A61B 8/5253; A61B 34/20; A61B 2034/2063
See application file for complete search history.

(56) References Cited

U.S. PATENT DOCUMENTS 6,045,508 A * 4/2000 Hossack ................. A61B 8/12
    600/447
6,443,896 B1    9/2002 Detmer
(Continued)

FOREIGN PATENT DOCUMENTS

WO    2015087191 A1    6/2015

OTHER PUBLICATIONS

Singh et al: "Development of an Ultrasound Imaging System for Needle Guidance"; 2009 IEEE International Ultrasonics Symposium Proceedings, pp. 1852-1855.
(Continued)

*Primary Examiner* — Serkan Akar
*Assistant Examiner* — Amal Aly Farag

(57) ABSTRACT

An ultrasound imaging system according to the present disclosure may include an ultrasound transducer assembly comprising a plurality of apertures that are configured to transmit signals toward and receive signals from a region of interest (ROI) of a subject, a tracking sensor disposed within the subject and configured to move within the ROI, the
(Continued)

sensor being responsive to signals transmitted by the apertures, and at least one processor in communication with the ultrasound transducer assembly and the tracking sensor. The at least one processor may be configured to generate a first image of a first portion of the ROI from signals received from at least one activated aperture, identify a position of the tracking sensor using signal data from the tracking sensor that corresponds to at least one signal transmitted by the apertures, and generate a second image of a second portion of the ROI from signals received from at least one other aperture activated based on the identified position, wherein the second portion of the ROI is different from the first portion of the ROI.

24 Claims, 9 Drawing Sheets

(52) U.S. Cl.
CPC .......... *A61B 8/4477* (2013.01); *A61B 8/4494* (2013.01); *A61B 8/5253* (2013.01); *A61B 34/20* (2016.02); *A61B 8/4488* (2013.01); *A61B 2034/2063* (2016.02)

(56) References Cited

U.S. PATENT DOCUMENTS

| | | | |
|---|---|---|---|
| 9,282,946 | B2 | 3/2016 | Vignon et al. |
| 2002/0130591 | A1 | 9/2002 | Fraser |
| 2008/0304729 | A1 | 12/2008 | Peszynski |
| 2009/0003675 | A1* | 1/2009 | Moreau-Gobard .. A61B 5/6828 382/131 |
| 2010/0063398 | A1 | 3/2010 | Halmann et al. |
| 2010/0262013 | A1 | 10/2010 | Smith et al. |
| 2012/0143063 | A1 | 6/2012 | Robinson |
| 2015/0141812 | A1 | 5/2015 | Stigall et al. |
| 2015/0359512 | A1 | 12/2015 | Boctor et al. |
| 2016/0143614 | A1* | 5/2016 | Huang ................. A61B 8/085 600/424 |

OTHER PUBLICATIONS

PCT/EP2018/050601 ISR and Written Opinion, dated May 29, 2018, 20 Page Document.

* cited by examiner

LARGE AREA ULTRASOUND TRANSDUCER ASSEMBLY AND SENSOR TRACKING FOR APERTURE CONTROL AND IMAGE GNERATION

CROSS-REFERENCE TO PRIOR APPLICATIONS

This application is the U.S. National Phase application under 35 U.S.C. § 371 of International Application No. PCT/EP2018/050601, filed on Jan. 11, 2018, which claims the benefit of U.S. Provisional Patent Application No. 62/448,067, filed on Jan. 19, 2017. These applications are hereby incorporated by reference herein.

RELATED APPLICATION

This application claims the benefit of and priority to U.S. Application No. 62/448,067, filed Jan. 19, 2017, which is incorporated by reference in its entirety.

TECHNICAL FIELD

This application relates to large area ultrasound transducer assemblies and corresponding methods.

BACKGROUND

Peripheral artery disease (PAD) is a common circulatory problem in which narrowed arteries reduce blood flow to the limbs. PAD leads to narrowing and hardening of the arteries. This causes decreased blood flow, which can result in pain, tissue injury and even tissue death. PAD is a common disorder that affects 8 to 12 million people in the US, especially those over 50. Besides medications, procedures such as angioplasty, stent placement, and bypass surgery may be necessary if the condition is severe (e.g., blood flow in the limb is completely or almost completely blocked). These procedures are often performed under X-ray guidance (fluoroscopy, arteriogram), which exposes the subject to radiation dose and contrast.

In patients with Chronic Total Occlusions (CTO), endovascular techniques require the use of guide-wires—long metal wires less than 1 mm in diameter—to cross the CTO (see e.g., FIGS. 6A and 6B, which show x-ray images of a femoral artery 604 before and after intervention). Following successful guide-wire crossing, therapies such as balloon dilatation or atherectomy are often used to expand or clear the vessel lumen. In these patients, the blocked region 603 and the segment of the vessel distal to the blocked region cannot be visualized with arteriogram (injection of contrast dye to visualize the vessel lumen under X-Ray, as shown by FIG. 6A). The use of pre-operative images obtained from MRI/CT is a possibility, but this increases cost and has other technical challenges such as image registration. Generally, FIG. 6A illustrates the problem with navigating CTO crossings under fluoroscopy. Because a portion of the vessel is blocked prior to treatment, the blocked portion of the vessel cannot be imaged using fluoroscopy. Furthermore, repetitive or extensive X-Ray radiation to radiation is undesirable. Thus, different techniques for guidance during intervention procedures, such as CTO crossings, may be desired.

External ultrasound has been explored alternative to fluoroscopy and angiography. While ultrasound beneficially does not require radiation or use of harmful contrast agents, current ultrasound equipment and techniques require a highly-skilled sonographer to continuous maneuver and manipulate an ultrasound transducer probe in order to continually image the interventional procedure (a typical ultrasound probe footprint (and therefore, the lateral width of the imaging FOV) is on the order of a few cm (~3-5 cm); hence the need to continually maneuver the probe when imaging lesions/occlusions that can often exceed 10 cm in length). In addition to being cumbersome, the requirement for a skilled sonographer renders ultrasound imaging impractical for CTO and other PAD interventions due to lengthy procedural times.

SUMMARY

The present invention provides systems and methods for ultrasound-guided interventional procedures. In certain aspects, the present invention provides techniques for externally imaging a vessel, which may span a distance over 10 cm, and in some cases 30 cm or more, for example, for use in diagnosis, treatment, and monitoring of PAD and other procedures.

An ultrasound imaging system according to the present disclosure may include an ultrasound transducer assembly comprising a plurality of apertures that are configured to transmit signals toward and receive signals from a region of interest (ROI) of a subject, a tracking sensor disposed within the subject and configured to move within the ROI, the sensor being responsive to signals transmitted by the apertures, and at least one processor in communication with the ultrasound transducer assembly and the tracking sensor. The at least one processor may be configured to generate a first image of a first portion of the ROI from signals received from at least one activated aperture, identify a position of the tracking sensor using tracking data from the tracking sensor generated responsive to at least one signal transmitted by the apertures, and generate a second image of a second portion of the ROI from signals received from at least one other aperture activated based on the identified position, wherein the second portion of the ROI is different from the first portion of the ROI. In some embodiments, the first and second portions of the ROI may be overlapping. In other embodiments, portions of the ROI may be non-overlapping. In some embodiments, the tracking sensor may include an ultrasound receiver, and the at least one processor may be configured to determine a location of the receiver with respect to an active aperture. In some embodiments, the at least one processor is configured to perform image segmentation, edge detection, contrast enhancement, or a combination thereof, and wherein activation of apertures is further based, in part, on the image segmentation, edge detection, contrast enhancement, or the combination thereof.

In some embodiments, the ultrasound imaging system may further include a multiplexer that is in communication with the at least one processor and the ultrasound transducer assembly and the multiplexer may be configured to selectively control the apertures based on the identified position of the tracking sensor. In some embodiments, the multiplexer may be configured to activate in response to the identified position, at least one aperture to transmit signals toward the ROI, and deactivate, in response to the identified position, at least one aperture from transmitting signals toward the ROI. In some embodiments, the multiplexer may be configured to communicatively couple only a single aperture to the imaging apparatus at any given time, and further configured to communicatively couple an aperture adjacent to a currently active aperture and to decouple the currently active aperture responsive to receipt of an indication of the tracking sensor approaching a boundary of or exiting the FOV of the currently active aperture. In some embodiments, the multiplexer may be configured to couple input signals associated with an aperture adjacent to a first side of a currently active aperture responsive to receipt of an indication of the tracking sensor approaching a boundary of or exiting the FOV of the currently active aperture. In some embodiments, the multiplexer may be configured to decouple input signals associated with an aperture adjacent to a second side opposite the first side of the currently active aperture responsive to receipt of the indication.

In some embodiments, the ultrasound transducer assembly may include a frame configured to enable each of the plurality of independently controllable apertures to be moved relative to one another to position the plurality of independently controllable apertures such that a field of view (FOV) of each of the plurality of independently controllable apertures includes a portion of the vessel. In some embodiments, the combined FOV of the ultrasound transducer assembly may have a length of 10 cm or greater. In some embodiments, the combined FOV of the ultrasound transducer assembly may have a length of 30 cm or greater. In some embodiments, the ultrasound transducer assembly may include a multi-patch array including a plurality of patches, and the frame may be configured to enable each of the plurality of patches to slide relative to one another. In some embodiments, the ultrasound transducer assembly may include a plurality of ultrasound probes, an array of each of the plurality of ultrasound probes providing respective one of the plurality of independently controllable apertures. In some embodiments, respective arrays of two adjacent apertures may be spaced by a gap, and the ultrasound imaging apparatus may include a transmit controller configured to steer beams of the respective arrays to image an intermediate region of the subject associated with the gap.

An ultrasound imaging system according to some embodiments may include an ultrasound transducer assembly comprising a plurality of independently controllable apertures, wherein each of the independently controllable apertures is configured to transmit signals to and receive signals from a region of interest (ROI) having a length from about 10 cm or greater, an ultrasound imaging apparatus coupled to each of the plurality of independently controllable apertures and configured to generate ultrasound images based on the received signals, a tracking sensor operatively associated with a tracking system and configured to be positioned on an interventional tool during an intervention procedure, and a multiplexer connecting each of the independently controllable apertures to the ultrasound imaging apparatus, wherein the multiplexer is configured to communicatively couple one or more of the plurality of independently controllable apertures to the ultrasound imaging apparatus based on tracking information received from the tracking system. In some embodiments, the ROI may have a length of up to about 50 cm.

A method of ultrasound imaging during an intervention procedure in accordance with some examples herein may include transmitting, using an ultrasound transducer assembly, ultrasound toward a region of interest (ROI) including a vessel, wherein the ultrasound transducer assembly comprises a plurality of independently controllable apertures, and wherein the transmitting includes transmitting ultrasound with at least one of the plurality of independently controllable apertures. The method may further include receiving echoes with the at least one of the plurality of independently controllable apertures, receiving, by at least one processor operatively associated with the ultrasound transducer assembly, tracking information from a tracking sensor positioned on an interventional tool in the vessel, activating another one of the plurality of independently controllable apertures based, at least in part, on the tracking information, and generating and displaying, responsive to the echoes, an ultrasound image of the ROI including the vessel.

In some embodiments, each of the independently controllable apertures may be movable relative to one another, and the method may further include adjusting a position of individual ones of the plurality of independently controllable apertures such that a field of view of each of the plurality of independently controllable apertures includes a portion of the vessel. In some embodiments, the ultrasound transducer assembly may include a plurality of ultrasound probes, and the positioning an ultrasound transducer assembly may include moving one or more of the plurality of ultrasound probes such that respective arrays of the one or more of the plurality of ultrasound probes are arranged to image at least a portion of the vessel. In some embodiments, the ultrasound transducer assembly may include a multi-patch transducer array, and the positioning an ultrasound transducer assembly may include moving one or more patches of the multi-patch array relative to other patches of the multi-patch array. In some embodiments, the activating another one of the plurality of independently controllable apertures may include receiving the tracking information by a multiplexer connecting each of the independently controllable apertures to the at least one processor, and communicatively coupling the another one of the plurality of independently controllable apertures to the at least one processor based on the tracking information. In some embodiments, the method may further include decoupling, by the multiplexer, a currently active aperture from the at least one processor when another one of the plurality of independently controllable apertures is activated. In some embodiments, the activating another one of the plurality of independently controllable apertures may include activating an aperture adjacent to one side of one or more currently active apertures and deactivating an aperture adjacent to the opposite side of the one or more currently active apertures. In some embodiments, the method may include imaging the vessel prior to advancing the interventional tool through the vessel to determine a target position for each of the apertures in which the respective apertures includes a portion of the vessel, and the target position may be maintained during the advancing of the interventional tool through the vessel.

Any of the methods in accordance with the present disclosure, or steps thereof, may be embodied in non-transitory computer-readable medium comprising executable instructions, which when executed may cause a processor of medical imaging system to perform method or steps embodied therein.

DESCRIPTION

Figure 1A:
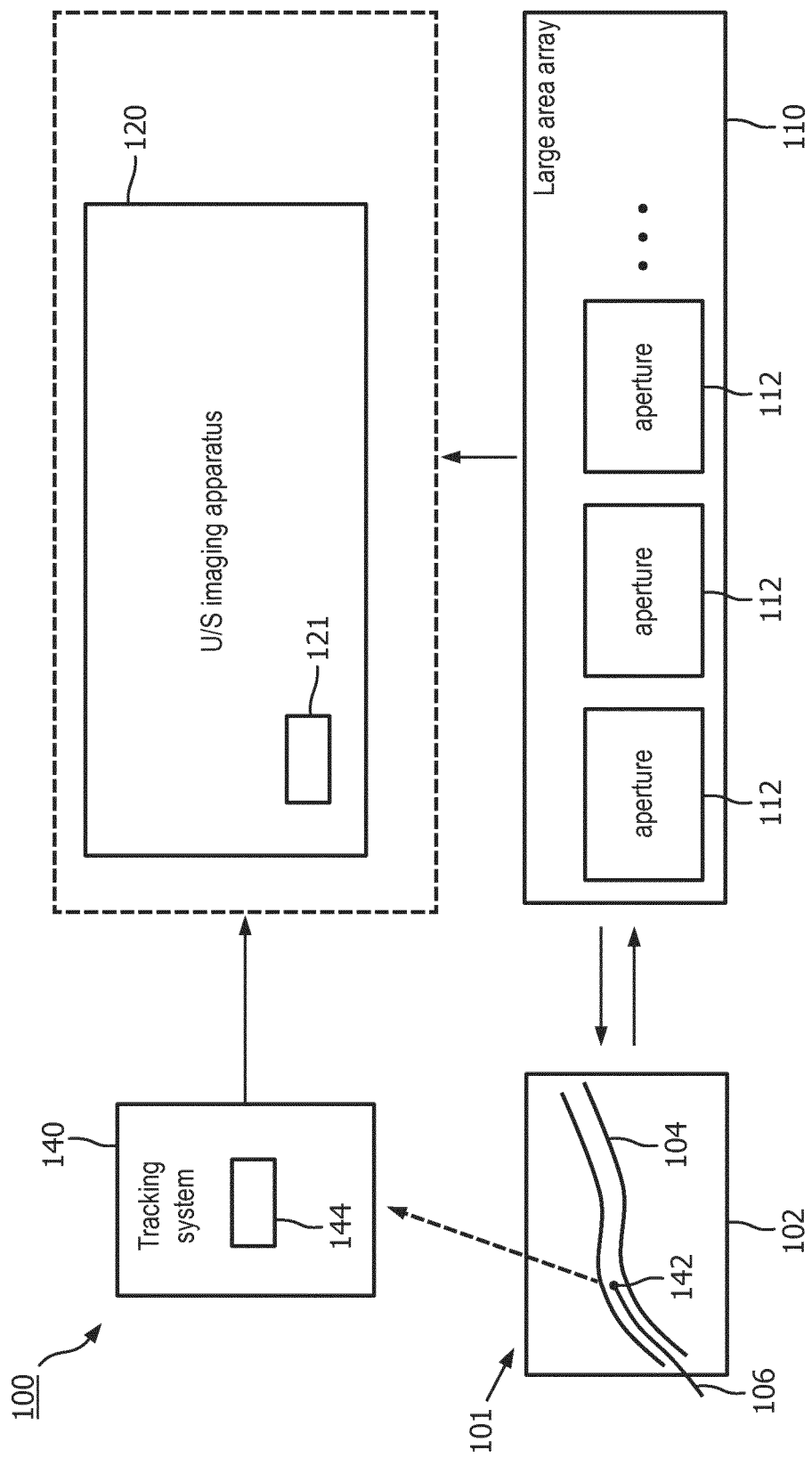
FIG. 1A is block diagram of an ultrasound system in accordance with the present disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

An ultrasound imaging system according to the present disclosure may include an ultrasound transducer assembly (also referred to herein as large area array), which includes a plurality of apertures that are configured to transmit signals toward a region of interest (ROI) of a subject and receive signals from the ROI. In some embodiments, the large area array may be controlled such that portions of the ROI may be overlapping, for example a first portion of the ROI imaged by one of the plurality of apertures may overlap a second portion of the ROI imaged by an adjacent one of the plurality of apertures. In some embodiments, the large area array may be controlled such that portions of the ROI are non-overlapping, for example the large area array may be controlled such that any one of the plurality of apertures images distinct, non-overlapping portion of the ROI. In some embodiments, the imaged portions of the ROI may be spaced or separated by a gap and information regarding the space between the imaged protons may be obtained through interpolation in accordance with known techniques.

The ultrasound imaging system may further include a tracking sensor configured to be disposed within the subject and movable within the ROI. For example, the tracking sensor may be attached to an interventional tool (e.g., a needle, guidewire, cannula, catheter, or the like). In some embodiments, the sensor may be responsive to signals transmitted by one or more active apertures. For example, the sensor may be an ultrasound receiver which is configured to detect ultrasound transmitted by an aperture of the large area array. In other embodiments, another type of tracking technology other than ultrasonic tracking may be used, for example electromagnetic (EM) tracking, in which case an EM sensor may be operatively associated with an EM field generator for tracking the position of the EM sensor within the EM field.

The ultrasound imaging system may further include at least one processor in communication with the ultrasound transducer assembly and the tracking sensor. The at least one processor may be part of a medical diagnostic system (e.g., an ultrasound imaging system). In some embodiments, certain functions of the at least one processor (e.g., the receipt and processing of tracking data) may be performed by a processor separate from the medical diagnostic system, such as a processor of a tracking system which is communicatively coupled to the medical diagnostic system. In some embodiments, the at least one processor may be configured to generate a first image of a first portion of the ROI from signals received from at least one activated aperture. For example, such functions of the at least one processor may be performed by one or more processors (e.g., signal processor, B-mode processor, Doppler processors, scan converter, graphics processor, etc.) of a medical diagnostic system.

In some embodiments, the at least one processor may be further configured to identify a position of the tracking sensor using tracking data from the tracking sensor generated responsive to at least one signal transmitted by the apertures. For example, in the case of ultrasonic tracking, the at least one processor, which may be part of ultrasound imaging system (e.g., a processor which may also be configured to perform other functions associated with medical imaging) or a separate processor communicatively coupled to the ultrasound imaging system may receive tracking data or signals from the tracking sensor responsive to ultrasound signals transmitted from an active aperture under the control of the ultrasound imaging system. The processor may perform, for example, one-way beam forming (e.g., accounting for the one-way travel time of ultrasound from the transmitting aperture to the receiving tracking sensor as opposed to typical pulse-echo beamforming as used for generating the images responsive to echoes received by an active aperture) to determine the position of the tracking sensor within the ROI.

In some embodiments, the at least one processor may be further configured to generate a second image of a second portion of the ROI from signals received from at least one other aperture activated based on the identified position of the tracking sensor, the second portion of the ROI being different from the first portion of the ROI. For example, the ultrasound imaging system may be configured to transmit signals toward and receive signals from a second portion of the ROI using another aperture of the large area array selected based on the position of the tracking sensor within the ROI. As the tracking sensor advances through the vessel and thus moves within the ROI, the processor may track the position of the sensor and controls the large area array to activate an aperture which includes the tracking sensor within its field of view. The active aperture may be any group of elements (e.g., a group of contiguous elements of a single large area array), which are selected electronically based on the position of the tracking sensor and thus based on the location of the interventional tool within the vessel. The active aperture may be electronically selected by the imaging system based on the tracking data. The size of the active aperture may depend on the number of available system channels and the desired image resolution. In some embodiments, the ultrasound imaging system may also be configured to display, for example, concurrently with, or on a same image as the anatomy) an indicator or image corresponding to the location of the tracking sensor. In some embodiments, and as will be described further below (e.g., with reference to FIGS. 2 and 3), the apertures may be physically separate apertures (e.g., arrays of individual probes or patches), which may be selectively coupled to an ultrasound imaging system using a multiplexer.

Figure 1B:
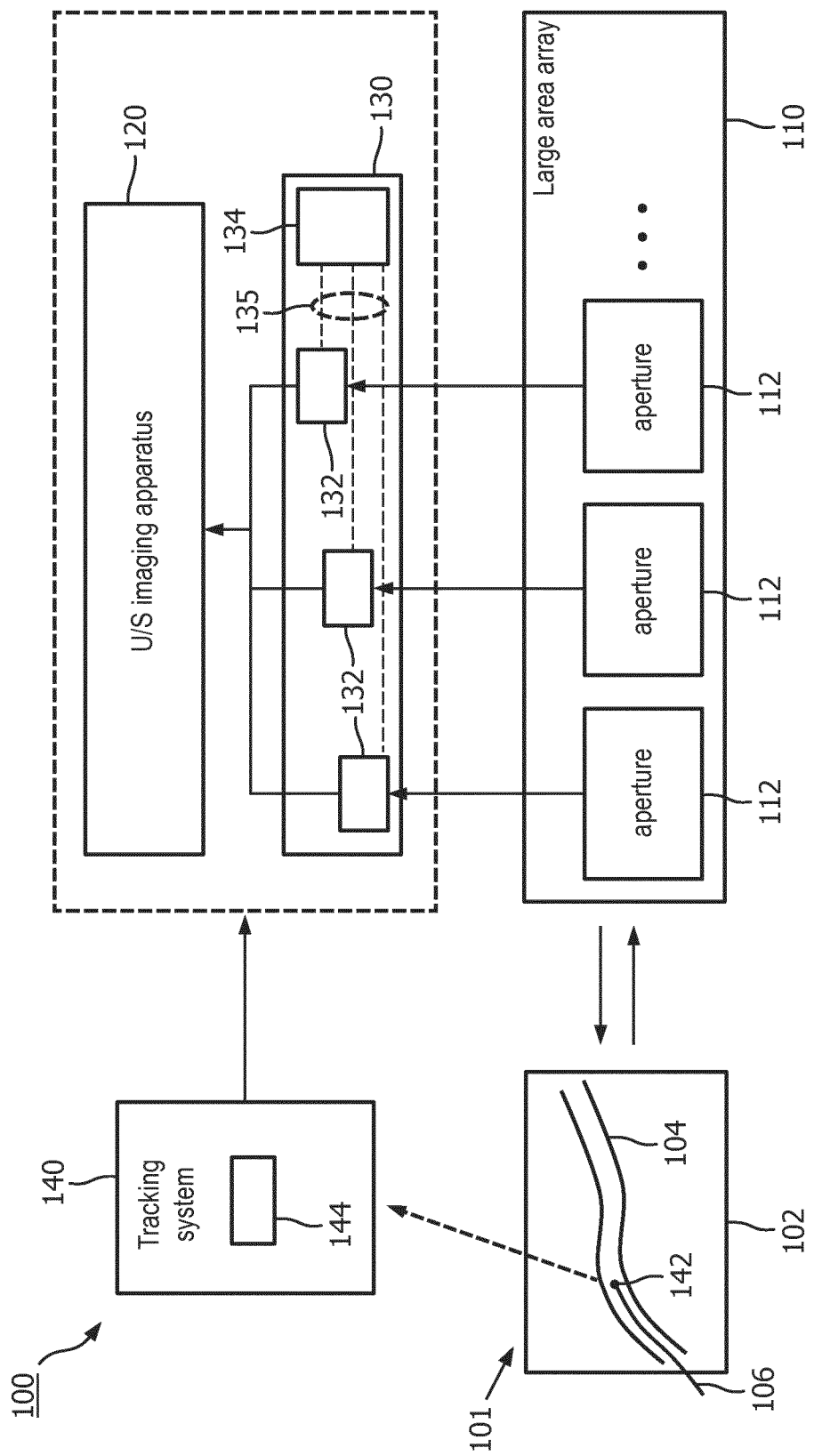
FIG. 1B is another block diagram of an ultrasound system in accordance with the present disclosure.

FIGS. 1A and 1B show block diagrams ultrasound systems in accordance with the present disclosure. Similar components in these block diagrams are designated using same reference numbers. The system 100 may include an ultrasound transducer assembly 110 (also referred to herein as large area array assembly or simply large area array), which includes a plurality of apertures 112. The system 100 may be configured to select an active aperture 112 from the plurality of apertures based on tracking information from a sensor positioned within the region of interest (ROI). In some examples, an active aperture may be formed by any subset of contiguous or adjacent elements of a large area array, e.g., as in the example in FIG. 1A. The size and or field of view of an active aperture may be electronically controllable by electronically selecting the subset of elements of the large area array to be activated (e.g., for transmission and reception). In some examples, each distinct aperture may be a sub-array of an ultrasound transducer assembly (e.g., an array of an individual probe or individual patch). In such examples, each distinct aperture may be selectively coupled to an imaging apparatus via a multiplexer, e.g., as in the example in FIG. 1B, and one or more of the apertures may be activated by activating one or more of the individual probes or patches, as will be described further below.

In some embodiments, one or more of the apertures 112 are independently controllable. By independently controllable it is generally implied that one or more apertures 112 are operable to transmit ultrasound and receive echoes independent of any other aperture in the transducer assembly 110. In other words, a fully beamformed ultrasound image may be obtained from any single one of the apertures 112 irrespective of whether imaging is performed by any other of the apertures at any given time. To that end, each individual aperture 112 is configured to be operatively coupled to beamforming and signal processing circuitry to produce an ultrasound image of the field of view provided by the given aperture. In one example, each of the apertures 112 is independently-controllable. In another example, a first set of apertures 112 may be controlled independently from a second set of apertures. The apertures 112 may be configured to transmit ultrasound toward and receive echoes from a region of interest (ROI) 102, which includes a vessel 104. In accordance with the examples herein, the independently controllable apertures 112 may be arranged in relation to the subject and one another such that each aperture includes at least a portion of the vessel 104 within its field of view (FOV). As such, each aperture 112 may provide a portion of the FOV of the combined or extended FOV of the large area array.

One or more apertures 112 of the assembly 110 may be positionally adjustable independent of other apertures in the assembly. In other words, the position and/or orientation of each sub-array of the large area array may be movable in relation to other sub-arrays so as to enable each individual sub-array may be positioned in relation to the subject such that the FOV of any of the sub-arrays includes at least a portion of the vessel to be imaged. The independently controllable apertures 112 may be adjustable along one, two or more degrees of freedom. In some examples, each of the independently controllable apertures may be movable in relation to an adjacent aperture along one translational direction (e.g., the elevation direction). By enabling the apertures to move in relation to one another, the transducer assembly may more effectively be able to follow the path of the vessel even when the vessel curves or changes direction along its length. In some examples, each of the independently controllable apertures may additionally or alternatively be movable in relation to an adjacent aperture along at least one rotational direction (e.g., pivoted about an axes passing through the interface between two adjacent apertures). By providing pivotal connection between adjacent apertures, the transducer assembly may more effectively be able to follow a contour of the surface of the subject upon which the large array is placed for imaging.

The system 100 may further include an ultrasound imaging apparatus 120 coupled to the plurality of apertures 112. The ultrasound imaging apparatus 120 may be configured to control the sub-arrays of the ultrasound transducer assembly 110 to transmit ultrasound waves and receive echoes for generating ultrasound images based on the echoes. The ultrasound imaging system may be operable for imaging in a variety of different modalities (e.g., B-mode, M-mode, PW Doppler, spectral Doppler, etc.). For example, certain functions of the ultrasound imaging apparatus 120 (e.g., certain functions for generating and displaying images) may be implemented in accordance with functionality of existing ultrasound machines, such as any one of the ultrasound machines provided by PHILIPS (e.g., VISIQ, SPARQ, EPIQ, or another ultrasound system).

The system 100 may include a tracking sensor 142 disposed within the subject and configured to move within the ROI 102. The sensor may be responsive to signals transmitted by the apertures 112. For example, the sensor 142 may include an ultrasound receiver. The sensor 142 may be communicatively coupled to at least one processor 121 of the system 100, which is in communication with the ultrasound transducer assembly 110. The at least one processor 121 may be configured to generate an image of a first portion of the ROI from signals received from at least one activate aperture, identify a position of the tracking sensor from data generated responsive to signals transmitted by at least one aperture, and generate another image of a second portion of the ROI from signals received from at least one other aperture activated based on the identified position of the tracking sensor. These functions can be performed by one or more processors of the ultrasound imaging apparatus 120 (e.g., processor 121), one or more processors of a tracking system 140 (e.g., circuitry 144), or combinations thereof.

In some embodiments, the tracking sensors 142 may be operatively associated with a tracking system 140. As shown, the sensor 142 may be positioned on an intervention tool 106 (e.g., a needle, guidewire or catheter) during an intervention procedure and the tracking system 140 may generate tracking information based on the location of the sensor 142 within a tracked field. The tracking sensor may include an ultrasound sensor, pressure sensor, or any other sensor responsive to ultrasound pulses emitted from the assembly 110. The tracking information may be transmitted to the multiplexer and/or the imaging apparatus 120 for selectively activating (e.g., via automatic electronic control) an appropriate aperture of the large array transducer. In this manner the system 100 may be configured to selectively activate one or more apertures 112 of the large area array based on the tracking information.

In some examples, the tracking system may utilize ultrasonic tracking to track a sensor 142 (e.g., an ultrasound receiver) positioned on the interventional tool 106. Preferably, the sensor 142 may be positioned on or proximate the tip of a needle or a catheter. In some embodiments, a plurality of tracking sensors are positioned along the length of the interventional device. In the case of ultrasonic tracking, the tracking system 140 may include separate beamforming circuitry 144 from the beamforming circuitry used by the ultrasound imaging apparatus 120. The beamforming circuitry 144 may be operable to perform one-way beamforming based on ultrasound received by the ultrasound receiver (e.g., the tracked sensor 142). By one-way beamforming, it is generally meant that the location of the receiver is determine based on one-way delays (e.g., one-way travel time) of the ultrasound for determining the distance and thus relative location of the receiver to the transmitter. The tracking sensor may be a passive ultrasound receiver (i.e., it only receives ultrasound from a transmitter, but does not transmit ultrasound), the imaging transducer (e.g., an active aperture of the large area array) functioning, in this case, as the transmitter. No additional transmit pulses may be needed for purposes of tracking. In other words, the tracking sensor may passively monitor, from within the ROI, the ultrasound signals that are transmitted for purposes of imaging and the location of the tracking sensor 142 may be determined by the beamforming circuitry 144. In some examples, the ultrasonic tracking system may be implemented in accordance with any of the examples in U.S. Pat. No. 9,282,946 titled "Ultrasonic tracking of ultrasound transducer(s) aboard an intervention tool," the disclosure of which is incorporated herein by reference in its entirety for any purpose. In some examples, beamforming of ultrasound signals received by the tracking sensor may be performed by beamforming circuitry provided in the ultrasound imaging apparatus 120 (e.g., by processor 121 which may be configured to perform one-way beamforming).

The tracking system 140 may determine, based on the tracking information (e.g., the location of the tracking sensor 142 in relation to an active aperture and/or intensity of the sensor signal), whether the tracking sensor 142 is within the field of view of the active aperture. For example, the stronger the signals received by the tracking sensor 142, the closer the tracking sensor 142 is to the focal zone (e.g., when using focused pulses of ultrasound for imaging) of the imaging beam. Generally, the location of the focused transmit beams are known and designed to cover the field of view (FOV) of each aperture. The number of transmit beams may vary from tens to several hundreds, depending on transducer type and imaging mode. For the purpose of ultrasonic tracking, the location of the interventional tool may be determined based, at least in part, on the strength of the signal received from the sensor (e.g., ultrasound receiver) attached to the interventional device. The signal strength may be strongest when the sensor is aligned with the transmit beam. As the interventional tool advances in the vessel, the location of the interventional tool may be determined in terms of which transmit beams correspond to the strongest signals received by the sensor. The relative location of the sensor within the FOV of any given active aperture may thus be determined and used to generate commands for activating and/or deactivating other apertures. For example, if the tracking system 140 determines that the sensor is aligned with the perimeter scan lines of the active aperture (as determined based on the known location of the transmit beams), the system (e.g., multiplexer 130) may activate the next probe ahead of the currently active aperture. In some examples, the perimeter scan lines may correspond from about 1 mm to about 3 mm, in some cases about 2 mm, of a FOV of about 4 cm in length, which may be achieved by a probe, for example, with about 320 transmit beams or a different number of beams. Additionally or alternatively, when the sensor is determined to be aligned with the perimeter scan lines and the sensor signal decreases at each frame, the multiplexer may activate the next probe in the array. Additionally or alternatively, the multiplexer may activate the next probe in the array once the signal fall off completely, which may correspond to the sensor leaving the FOV of the active aperture.

In this manner, the tracking system 140 may be configured to determine that the tracking sensor is approaching the boundary of the FOV, e.g., responsive to an indication of a decrease in the signal, or it may determine that the tracking sensor has exited the FOV responsive to failure to detect any signal with the receiver. The tracking system may generate a command for activating the next aperture along the travel path of the interventional tool responsive to a determination that the tracking sensor is approaching the boundary of or has exited the FOV of the active aperture.

In further examples, the tracking system 140 may be an electromagnetic (EM) tracking system which may be operable to localize each of the apertures 112 and the tracking sensor 142 in relation to a single reference frame. The apertures 112, the subject being imaged 101, and correspondingly the interventional tool 106 (e.g., needle) being tracked during an intervention procedure, may be located within a tracked field (e.g., an EM field) and the tracking system may be configured to determine the location (e.g., a position and/or orientation) of each tracked object within the tracked field. Once the location of each tracked object is determined in relation to the reference frame, the locations of each of the tracked objects relative one another and in relation to the reference can be determined. Based on this relative localizing of tracked objects within the tracked field, the tracking system 140 may determine when the tracking sensor enters and exits the field of view, and correspondingly, is within the FOV, of a given aperture. This information can be used to provide activation commands (e.g., generate a select signal for operating the switching circuitry of the multiplexer) to selectively couple and decouple signal lines of one or more apertures of the large area array 110.

In some embodiments, e.g., as shown in FIG. 1B, the ultrasound imaging apparatus 120 may be coupled to the apertures 112 via a multiplexer 130. The multiplexer 130 may be configured to selectively communicatively couple any one (or more) of the apertures 112 to the imaging apparatus 120 based on tracking information from the sensor 142 positioned on the interventional tool 106. In some examples, the multiplexer 130 may be configured to receive the tracking information and couple and/or decouple input signals of one or more apertures to the output channels of the multiplexer responsive to select signals generated based on the tracking information. In some examples, multiple apertures can be activated simultaneously, e.g., if larger FOV imaging is desired in real-time. For example, if the sensor is deemed to be in the FOV of the second aperture of the array, apertures 1, 2, and 3 may be activated. As the sensor moves into the FOV of the third aperture, then apertures 2, 3 and 4 may be activated, and so on.

For example, the multiplexer may include a plurality of switches 132, each of which is coupled to one of the apertures 112. The multiplexer 130 may also include a selector circuit 130 which is configured to generate the select signals for operating the switches 132. For example, the selector circuit 130 may receive data, generated by the tracking system 140 based on tracking information from sensor 142, which may be indicative of whether the tracking sensor 142 is within the field of view of a current active aperture (i.e., an aperture communicatively coupled to transmit and receive signals from the imaging apparatus 120). Based on the data, the selector circuit 130 may generate one or more select signals 135. The select signal(s) may be configured to close a switch associated with the next aperture if the data indicates that the tracking sensor is outside of the FOV of the currently active aperture. In some examples, the select signal(s) may be further configured, responsive to an indication that the tracking sensor is outside of the FOV of the currently active aperture, to open a switch associated with currently active aperture or an aperture preceding the currently active aperture to deactivate the currently active aperture or an aperture preceding the currently active aperture. The terms next and preceding (or equivalently ahead of and behind) are generally used herein in imply relative location of apertures with relation to the travel path of the interventional tool (e.g., next being the aperture forward of the currently active aperture along the path of travel of the interventional tool and preceding being the aperture before the currently active aperture along the path of travel of the interventional tool) and are not meant to be limiting in any other way.

In some embodiments, the multiplexer may be configured to communicatively couple only a single aperture to the imaging apparatus 120 at any given time. One advantage of this may be that any conventional ultrasound imaging system, which is configured to operate with a single probe, may be used to implement principles of the present disclosure. Thus, when the active aperture is determined to no longer include the tracking sensor within its field of view, the multiplexer 130 may be configured to communicatively couple the next aperture to while decoupling the currently active aperture from the imaging apparatus 120 and the image display would then refresh (e.g., when displaying in real-time) to show the FOV of the newly activated aperture in the place of the previously active aperture.

In some embodiments, the multiplexer may be configured to communicatively couple multiple apertures the imaging apparatus 120 at any given time. This can be achieved with a data link between the multiplexer and imaging apparatus 120 which includes a high channel count (e.g., a larger number of inputs than needed for receiving signals from a single probe). In some examples a parallel data link may be used, which may enable the imaging apparatus 120 to simultaneously receive echo information from multiple and in some case all of the apertures of the array 110. In some examples, a subset of the apertures but not all of the apertures of the array 110 may be communicatively coupled. For example, apertures that are farthest apart (e.g., farthest ahead, or farthest behind) from the current location of the tracking sensor (e.g., which may indicate the current location of the tip of the interventional tool) may be deactivated, e.g., to reduce use of computational resources. As the interventional tool is advanced in the vessel, one or more apertures ahead of any currently active apertures may be activated and one or more apertures behind the currently active apertures may be deactivated. In some embodiments, some or all functions of the selector circuit 134 may be implemented in circuitry (e.g., processor 460 of system 400 described further below) which may be provided elsewhere other than the multiplexer (e.g., in the imaging apparatus), and the multiplexer may automatically switch between apertures responsive to commands from the processor 460. In this manner, the multiplexer may be configured to selectively communicatively couple one or more of the plurality of independently controllable apertures to the imaging apparatus based on tracking information received from the tracking system. By automatically (e.g., electronically) moving the aperture along the length of the array and thus along the length of the vessel, the system obviates the need for physically moving a probe during the guidance procedure as was needed with conventional system, which may not only simplify the clinical workflow, but may also reduce artifacts in the images (e.g., in panoramic views obtained from and while physically moving a probe).

Figure 2A:
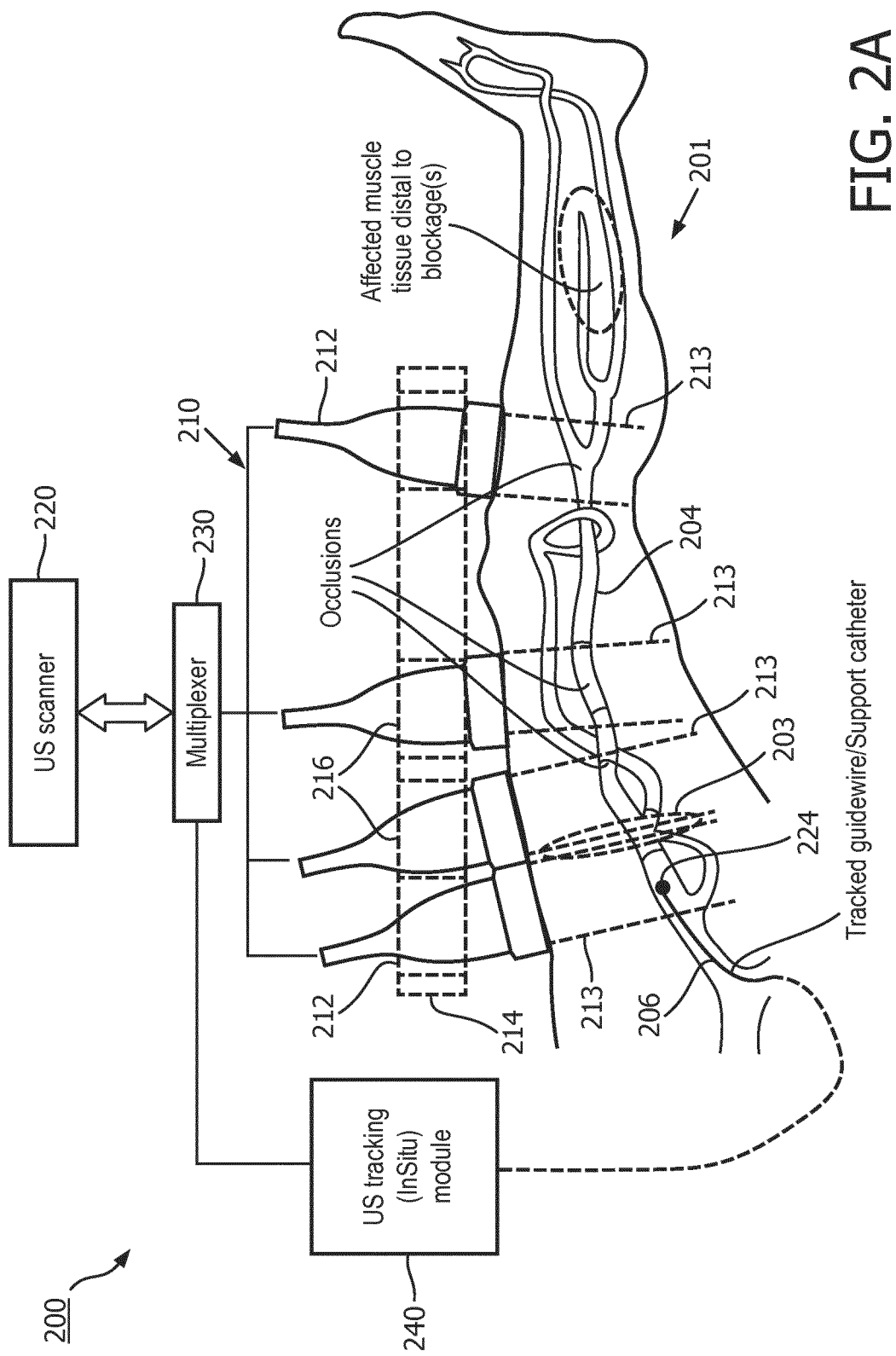
FIG. 2A is an illustration of an embodiment of an ultrasound system in accordance with the present disclosure.

FIG. 2A shows an illustration of an ultrasound system in accordance with further examples of the present disclosure. The system 200 includes an ultrasound transducer assembly 210, an ultrasound imaging apparatus 220, a tracking sensor 242, and a multiplexer 230.

In the example in FIG. 2A, the ultrasound transducer assembly 210 is implemented using a plurality of ultrasound probes 212, and the array of each individual probe may correspond to one of the independently controllable apertures of the large area array. Each of the probes may include a 1D or 2D array operatively associated with circuitry (e.g., application specific integrated circuit ASIC) for operation of the probe's array, as is conventionally known, and the components of which may be at least partially enclosed by a housing. Each of the probes 212 may be independently operable (e.g., when coupled to an imaging apparatus) to produce an ultrasound image (e.g., a B-mode, a color flow Doppler, or spectral Doppler image). In the example in FIG. 2A, the probes 212 may be held in place (e.g., maintained in a desired position with respect to one another and/or the subject) using a gantry or frame 214. The frame 214 may include a corresponding number of holding components 216, which may be adjustable to enable each probe 212 to be independently positioned in relation to other probes in the assembly 210. For example, the frame may enable each aperture to be moved laterally (e.g., perpendicular to the vessel) and pivoted (i.e., to change the angle of the nominal imaging plane of each aperture) for optimal orientation of an aperture in relation to the vessel.

The probes 212 may be manually positioned (e.g., prior to the invasive procedure) or electronically positioned (e.g., responsive to commands sent to the holding components 216) such that the FOV 213 of the array of each probe includes at least a portion of the vessel 204 of subject 201. In some examples, the probes 212 may be manipulated (e.g., positionally adjusted) until the imaging plane of the array is at an optimal orientation with respect to the vessel, e.g., the imaging plane intersects the vessel along most or all of the length of the vessel portion which is within the FOV 213 of the array. This may be performed prior to the intervention procedure and the imaging performed by the plurality of probes prior to the intervention procedure may be used to generate a model of the vessel, which may be used for further guidance during the intervention procedure. In some examples, the optimal orientation of the probes may be further determined based on signal strength from the tracking sensor 242. In such examples, the probes may be further adjusted to a position in which the strongest signal is detected when the tracking sensor is within the FOV 213 of a given probe.

The tracking sensor 224 may be operatively associated with a tracking system 240, which in this case may be an ultrasonic tracking system. Thus, the sensor 224 may be implemented using an ultrasound receiver or other sensor, as described previously with regards to FIGS. 1A and 1B. The tracking system 240 may be configured to receive tracking information from the sensor 224 for determining the location of the sensor in relation to one or more of the probes 212. In the snapshot in time shown in FIG. 2A, the sensor 224 is located within the FOV 213 of the first of the plurality of probes 212. Thus, the tracking system 240 may be configured to send data to the multiplexer 230 indicative that the sensor 242 remains within the tracking field for the first probe. As the interventional tool 206 advances along the vessel 204, the sensor 242 will exit the field of view of the first probe to then enter the FOV 213 of the second one of the plurality of probes 212. As the sensor 242 approaches the boundary (e.g., the last few scan lines) of the FOV of the first probe, or upon exit of the sensor 242 from the FOV of the first probe, the tracking system 240 may transit corresponding data to the multiplexer, which may generate a command for activating the second probe. Responsively, select signals may be applied to switching circuitry of the multiplexer to communicatively couple the second probe to the imaging apparatus 220. Additionally and optionally (e.g., in the case where the imaging apparatus 220 is operable to receive echo information from only one aperture at a time), the multiplexer 230 may generate a command for deactivating the first probe. Responsively, select signals may be applied to switching circuitry of the multiplexer to communicatively decouple the first probe from the imaging apparatus 220. This process of automatic electronic movement of the aperture along the length of the array 210 may continue during the intervention procedure to track the movement and thus continue to image the interventional tool as it advances along the length of the vessel 204. While only four probes are shown in FIG. 2A, for illustration only, it will be understood that any (e.g., fewer or more than four) number of probes may be used in some examples.

Figure 2B:
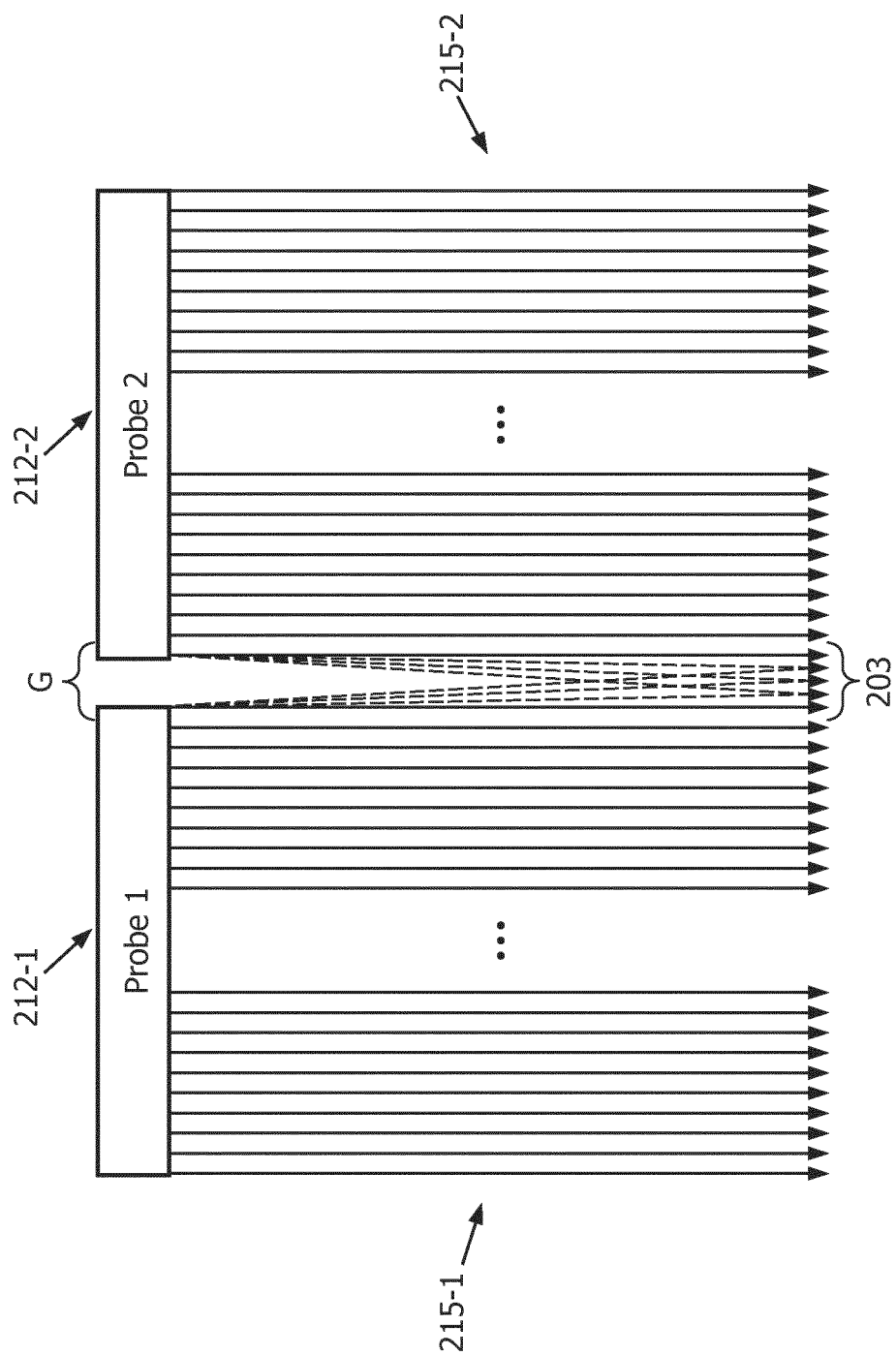
FIG. 2B is an illustration of adjacent apertures of an ultrasound system in accordance with the present disclosure, and more specifically illustrates beam steering as may be used to image the region between the FOV of the adjacent apertures.

The probes may be equipped with any type of array (e.g., linear, curved, phased, etc.) as may be suitable for a particular application. As illustrated in FIG. 2A, the individual probes 212 may have linear arrays. When linear arrays are used, due to the physical spacing between the arrays (e.g., as caused by mechanical components and/or the enclosure of each probe), a gap G (see also FIG. 2B) may exist between the FOVs of the adjacent probes. The region of the subject that's associated with the gap (e.g., intermediate region 203) may thus be outside of the field of view of any of the probes a present in a blind spot during the imaging and intervention procedure. As shown further in FIG. 2B, beam steering may be used to image the regions associated with any gaps G between adjacent apertures (e.g., probes 212-1 and 212-2 of FIG. 2B). As shown in FIG. 2B, when scanning the last few lines in the image plane 215-1 of the first probe, the beams transmitted from the first probe 212-1 may be steered (e.g., anywhere between 5 to 15 degrees) towards the second probe 212-2 to cover the intermediate region 203. Similarly, when scanning the first few lines in the image plane 215-2 of the second probe 212-2, the beams may be steered (e.g., anywhere between 5 to 15 degrees) towards the preceding probe (probe 212-1) to cover the intermediate region 203, thus removing any blind spots from the combined FOV of the transducer assembly. In some embodiments, e.g., based on the probes used, the gap G between adjacent apertures may be anywhere between 2 mm-5 mm, but typically not exceeding 1 cm. In some embodiments, each individual aperture may provide a FOV of about 4 cm in length (e.g., along the length of the vessel), which may amount to a combined FOV for the large area array of 10 cm or greater (e.g., in the case of 4 probes, about 16 cm in length, and in the case of a greater number of probes 30 cm or greater). In some examples, the individual probes may have curvilinear or sector arrays, the scan lines of which may fan out from the nominal axial direction (e.g., normal to the center of the array) and thus may provide overlapping FOV thus eliminating any blind spots.

Figure 3A:
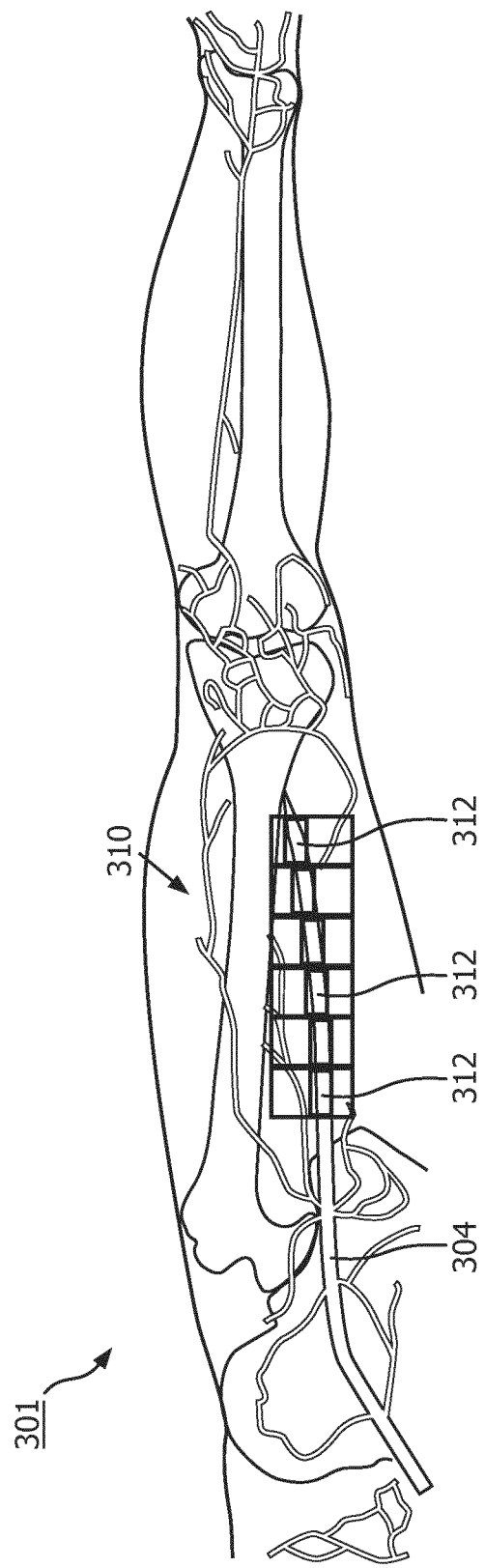
FIGS. 3A and 3B show is illustrations of another embodiment of an ultrasound system in accordance with the present disclosure.
Figure 3B:
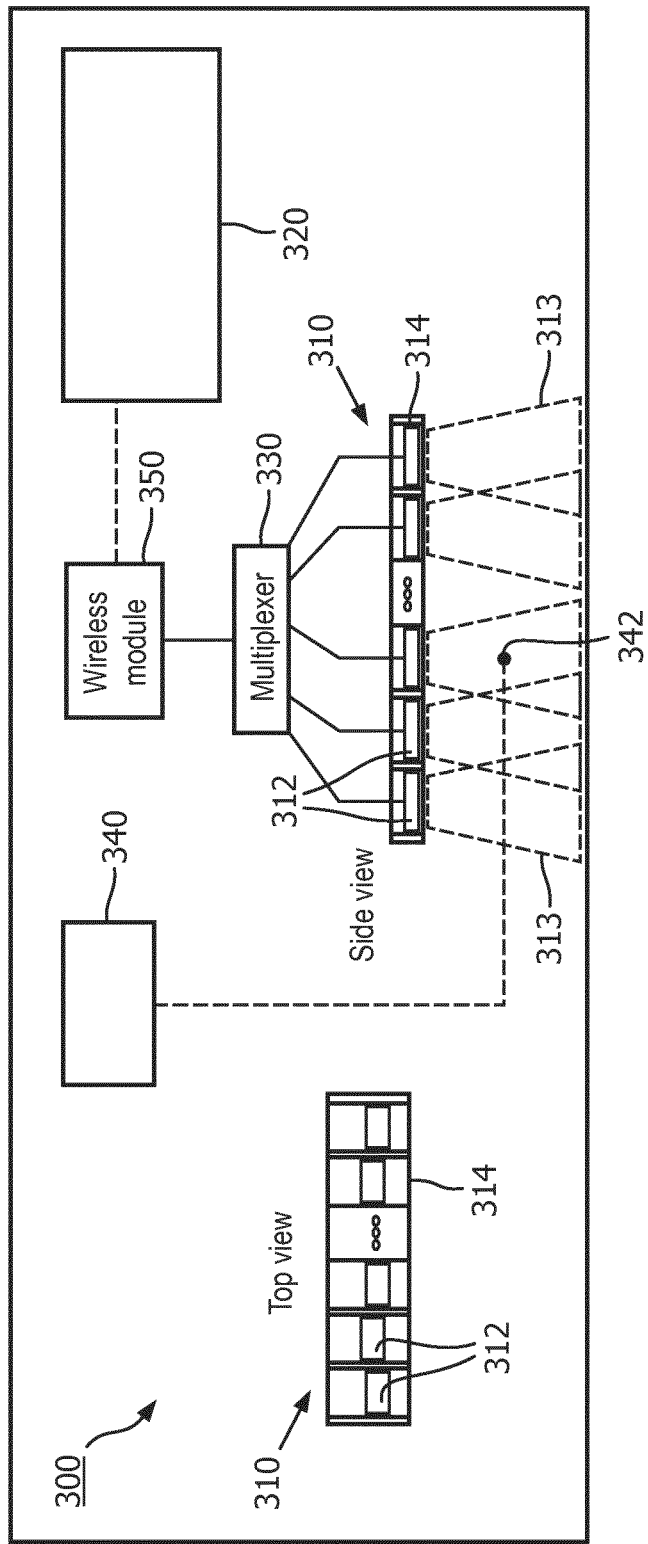

FIG. 3A shows an illustration of an ultrasound system 300 in accordance with further examples of the present disclosure and FIG. 3B shows an illustration of a use case for the array in FIG. 3A. The system 300 includes an ultrasound transducer assembly 310, an ultrasound imaging apparatus 320, a sensor 342, and a multiplexer 330. The tracking sensor 342 may be attached to an interventional device (e.g., a guidewire) which may be inserted in a vessel 304 (e.g., a femoral artery) during an intervention procedure (e.g., a CTO crossing). In the example in FIG. 3A, the ultrasound transducer assembly 310 is implemented using multi-patch array 310. The multi-patch array 310 includes a plurality of individually adjustable patches 312, each of which correspond to one of the independently controllable apertures of the large area array. Each of the adjustable patches 312 includes a 1D or 2D array of transducer elements. Each of the patches 312 may have a length (e.g., along the azimuth of the multi-patch array 310) of about 3-5 cm and may thus provide a FOV 313 of at least about 3-5 cm. The adjustable patches 312 are connected by frame 314, which is configured to enable the patches to move relative to one another. For example, the individual patches 312 may be slidably (e.g., frictionally or otherwise) coupled to enable each patch 312 to slide in the elevation direction. In some examples, the patches may alternatively or additionally be pivotable along the interface between adjacent patches to enable the array 310 to be wrapped around a contoured surface. In some examples, the array 310 may be implemented in accordance with any of the examples of co-pending application titled "Multi-patch array, ultrasound system, and method for obtaining an extended field of view," the disclosure of which is incorporated herein by reference in its entirety for any purpose.

The imaging apparatus 320 may include one or more components of ultrasound imaging system described herein (e.g., ultrasound imaging system 400 described further below with reference to FIG. 4). The imaging apparatus 320 may be configured to generate an ultrasound image from echoes received by the multi-patch array 310. The imaging apparatus 320 may be a highly portable device. For example, the imaging apparatus 320 may be an ultrasound imaging system implemented on a hand-held device (e.g., tablet, smartphone, etc.) such as the VISIQ or LUMIFY ultrasound systems provided by PHILIPS). In some examples, the imaging apparatus 320 may be an ultrasound imaging system implemented in a more conventional form factor, e.g., as larger but still typically portable base, which may provide a variety of imaging functions (e.g., B-mode, M-mode, color flow Doppler, PW Doppler, spectral Doppler, and other ultrasound imaging modes). For example, the imaging apparatus 320 may be an ultrasound imaging system such as the SPARQ or EPIQ ultrasound systems provided by PHILIPS. Other ultrasound systems may be used.

The array 310 may be coupled to the imaging apparatus 320 via a multiplexer 330, which may be configured to selectively couple each of the plurality of patches to the imaging apparatus 320. The multiplexer 330 may have some or all of the functionality of any of the multiplexers described herein (e.g., multiplexer 130). As described, in some examples, the multiplexer 330 may be configured to communicatively couple only a single one of the plurality of patches to the imaging apparatus 320 at any given time. Thus, responsive to tracking information from sensor 342 and tracking system 340, the multiplexer 330 may activate a patch ahead of a currently active patch and deactivate the currently active patch (e.g., based on a determination that the sensor is approaching the end or is outside of the FOV of the currently active patch). In some examples, the multiplexer 330 may be connected to an imaging apparatus 320 having a high channel count and may thus be configured to communicatively couple multiple ones of the plurality of patches to the imaging apparatus 320 at any given time. The multiplexer 330 may be connected to each of the individual patches, via a wired or a wireless connection, and may be configured to perform a switching function as described herein to selectively couple one or a subset of the plurality of patches 312 to the imaging apparatus 320. In further examples, the multiplexer 330 may be connected, via a wired (e.g., a USB cable, not shown) or wireless connection (e.g., wireless module 350), to the imaging apparatus 320 for transmitting the echo information form an active patch to the imaging apparatus 320.

As described, the system 300 may selectively couple one or more of the patches 312 to the (imaging apparatus 320 based on tracking information from the tracking sensor 342 positioned on an interventional tool. The tracking information may be provided by an ultrasonic tracking system or an electromagnetic (EM) tracking system, as described with reference to FIGS. 1A and 1B, or another type of tracking technology currently known or later developed. For example, in the case of ultrasonic tracking, the tracking system 340 may estimate the position of a passive ultrasound sensor (e.g., PZT, PVDF, copolymer or other piezoelectric material) in the field of view (FOV) of a an ultrasound transducer patch by analyzing the signal received by the tracking sensor as the beams of the imaging probe sweep the FOV. Time-of-flight measurements may provide the axial/radial distance of the tracking sensor from the imaging array, while amplitude measurements and knowledge of the beam firing sequence may provide the lateral/angular position of the sensor. When used with 3D transducers (i.e., 2D matrix arrays), the elevational position of the tracking sensor can also be obtained in a similar manner. Therefore, the 3D position of the tracking sensor can be estimated in real-time, provided it is present within the FOV of the imaging probe. The tracking sensor can be deposited on any interventional tool such as a needle, a cannula, a catheter, a guidewire, etc. It will be understood that ultrasonic tracking of the type described in the context of the multi-patch array 310 may be utilized with any type of large area array (e.g., arrays 110, 210) of the present disclosure.

Aside from position information obtained from the tracking system, the relative position of each patch 312 in the array 310 may be easily determined using position sensors associated with each patch. For example, position sensors (e.g., linear encoders) may be used to determine the relative position of each patch to the frame when the patches are adjusted to obtain optimal view. Also, as described with regards to the multiple probe transducer assembly, because the relative position of each aperture, in this case each patch, is known, the relative position of objects in the images acquired with each probe during the intervention procedure may be determined. In some example, images from adjacent aperture may be fused for generating a combined image of the extended field of view provided by the large area array. In some examples, the amount of travel of the interventional tool (e.g., needle) within the vessel may be estimated based on the co-registration of the apertures (e.g., relative positional information of the apertures). For example, if the first aperture in the array is considered the reference aperture, the location of the needle when visualized using the first aperture may be considered the reference location. As the interventional tool is advanced and because the relative position of the other apertures in relation to the first aperture is known, the distance traveled by the needle (e.g., 7 cm, 8 cm, and so on) can be computed in relation to the reference location and this information can be provided as further guidance to the user during the intervention procedure.

Figure 4:
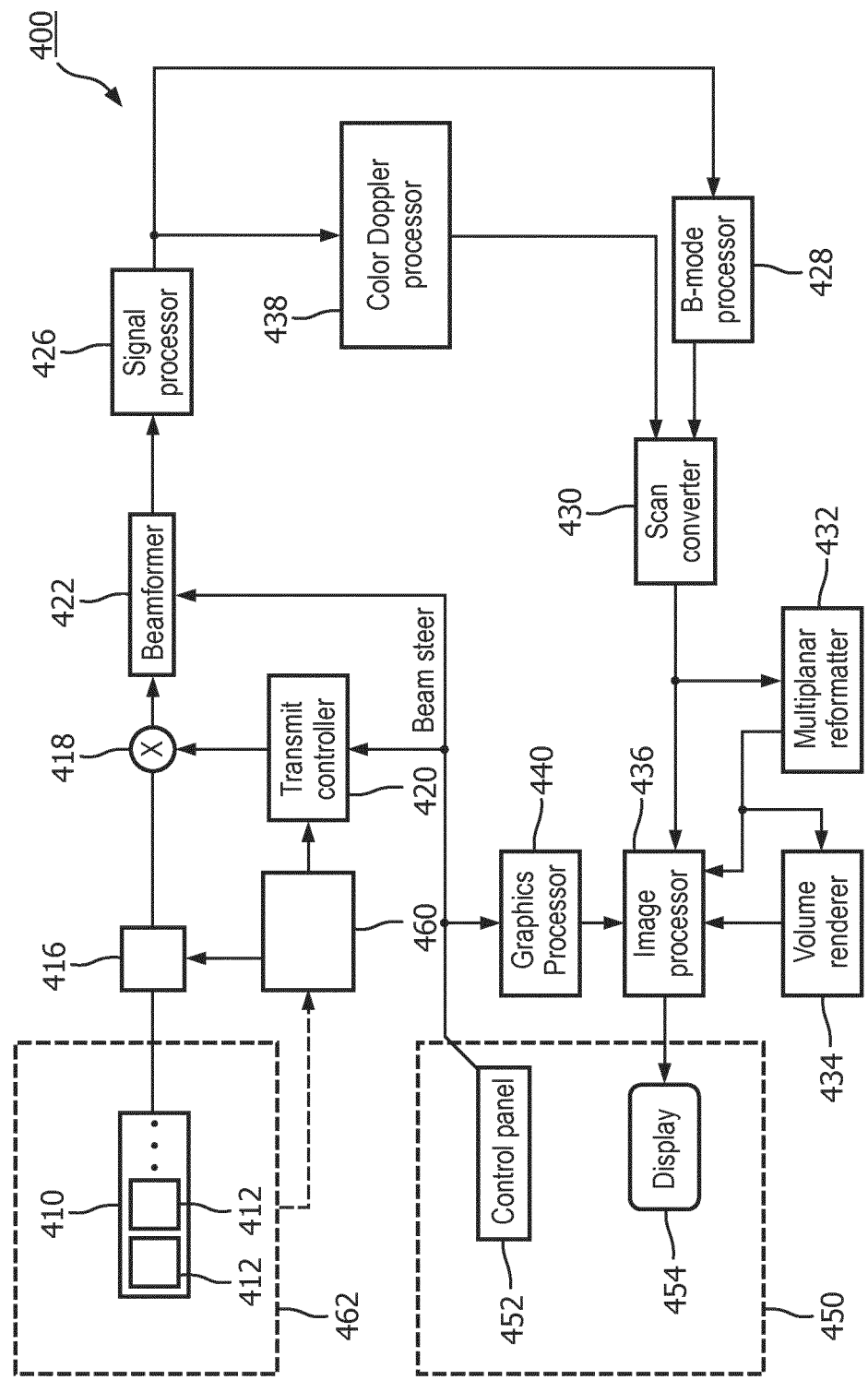
FIG. 4 is another block diagram of an ultrasound system in accordance with the present disclosure.

FIG. 4 shows a block diagram of an ultrasound system 400 according to the present disclosure. Some or all of the components of system 400 may be used to implement any of the imaging apparatuses described herein (e.g., ultrasound imaging apparatus 120 of FIG. 1A or 1B). The ultrasound system 400 may be configured to be coupled to a transducer array 410, which may include a plurality of independently controllable apertures 412. Each of the apertures 412 is operable to transmit ultrasound toward a region of interest including a vessel of a subject and to receive echoes for imaging the vessel. The term aperture may be used to refer to a group or set of transducer elements operable to obtain image data of a portion of a region of interest, irrespective of whether the apertures are part of a single array or are distinct arrays of individual probes or patches. A variety of transducer arrays may be used for the apertures, e.g., linear arrays, curved arrays, or phased arrays. The individual apertures 412 may include, for example, a two dimensional array of transducer elements capable of scanning in both elevation and azimuth dimensions for 2D and/or 3D imaging. The apertures (e.g., the individual probes 212 of FIG. 2, or the patches 312 of FIG. 3) may be movable relative to one another to arrange the apertures in relation to the subject such that the field of view of each aperture includes at least a portion of the vessel. For example, the array 410 may be implemented using any of the transducer assemblies described herein (e.g., array 210 or 310).

The apertures 412 may be coupled to microbeamformers, which may be located on the array 410 or in an ultrasound system base, which may control the transmission and reception of signals by the sub-arrays of each patch. In some examples (e.g., in the case of individual sub-arrays of probes or patches), the array 410 may be coupled to the ultrasound system base via a multiplexer 416 which may be coupled (via a wired or wireless connection) to a transmit/receive (T/R) switch 418 in the base. The multiplexer may selectively couple one or more of the patches 412 to the base (e.g., to the beamformer 422). The T/R switch 418 may be configured to switch between transmission and reception, e.g., to protect the main beamformer 422 from high energy transmit signals. In some embodiments, the functionality of the T/R switch 418 and other elements in the system may be incorporated in the multiplexer 416.

The multiplexer 416 may selectively couple one or more apertures 412 of the array 410 responsive to tracking data from a tracking sensor (not shown). The system 400 may include at least one processor 460, which is operable to determine the position of the sensor in the region of interest being imaged and control the activation of apertures 412 of the array. In some examples, the processor 460 may be configured to receive tracking data from a tracking system 462 operatively associated with a tracking sensor within the field of view of the array 410 and generate commands for activating and/or deactivating apertures of the array 410 based on the tracking data. For example, the processor 460 may include functionality of the beamforming circuitry 144 of tracking system 140 described above. The processor 460 may send commands to the multiplexer 416, if used, or to the transmit controller 420 and/or T/R switch 418 for selectively activating elements of the array 410. Additionally, image processing techniques (e.g., image segmentation, edge detection, contrast enhancement, combinations thereof or other image processing techniques) which may be performed by the processor 460 or other processing components of the ultrasound system 400, may be used for example to determine the presence of the interventional tool and/or identify the tip of the interventional tool, and thus may be used as further input for selecting an active aperture. The ultrasound system base typically includes software and hardware components including circuitry for signal processing and image data generation as well as executable instructions for providing a user interface.

The transmission of ultrasonic pulses from an active sub-array (e.g., from an active aperture 412) may be directed by the transmit controller 420 coupled to the T/R switch 418 and the beamformer 422, which may receive input from the user's operation of a user interface 450. The user interface 450 may include one or more input devices such as a control panel 452, which may include one or more mechanical controls (e.g., buttons, encoders, etc.), touch sensitive controls (e.g., a trackpad, a touchscreen, or the like), and other known input devices. Another function which may be controlled by the transmit controller 420 is the direction in which beams are steered. Beams may be steered straight ahead from (orthogonal to) the transmission side of the array 412, or at different angles for a wider field of view. The beamformer 422 may combine partially beamformed signals from groups of transducer elements of the individual patches into a fully beamformed signal. The beamformed signals may be coupled to a signal processor 426.

The signal processor 426 can process the received echo signals in various ways, such as bandpass filtering, decimation, I and Q component separation, and harmonic signal separation. The signal processor 426 may also perform additional signal enhancement such as speckle reduction, signal compounding, and noise elimination. The processed signals may be coupled to a B-mode processor 428 for producing B-mode image data. The B-mode processor can employ amplitude detection for the imaging of structures in the body. The signals produced by the B-mode processor 428 may be coupled to a scan converter 430 and a multiplanar reformatter 432. The scan converter 430 is configured to arrange the echo signals in the spatial relationship from which they were received in a desired image format. For instance, the scan converter 430 may arrange the echo signal into a two dimensional (2D) sector-shaped format, or a pyramidal or otherwise shaped three dimensional (3D) format. The multiplanar reformatter 432 can convert echoes which are received from points in a common plane in a volumetric region of the body into an ultrasonic image (e.g., a B-mode image) of that plane, for example as described in U.S. Pat. No. 6,443,896 (Detmer). A volume renderer 434 may generate an image of the 3D dataset as viewed from a given reference point, e.g., as described in U.S. Pat. No. 6,530,885 (Entrekin et al.).

Additionally, the signals from the signal processor 426 may be coupled to a Doppler processor 438, which may be configured to estimate the Doppler shift and generate Doppler image data. The Doppler image data may include color data which is then overlaid with B-mode (or grayscale) image data for display. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some examples, the velocity and power estimates may undergo threshold detection to reduce noise, as well as segmentation and post-processing such as filling and smoothing. The velocity and power estimates may then be mapped to a desired range of display colors in accordance with a color map. The color data, also referred to as Doppler image data, is then coupled the scan converter 430 where the Doppler image data is converted to the desired image format and overlaid on the B mode image of the tissue structure containing the blood flow to form a color Doppler image.

Output (e.g., images) from the scan converter 430, the multiplanar reformatter 432, and/or the volume renderer 434 may be coupled to an image processor 436 for further enhancement, buffering and temporary storage before being displayed on an image display 454. A graphics processor 440 may generate graphic overlays for display with the images. These graphic overlays can contain, e.g., standard identifying information such as patient name, date and time of the image, imaging parameters, and the like. For these purposes the graphics processor may be configured to receive input from the user interface 450, such as a typed patient name or other annotations. In some embodiments, the ultrasound system 400 may also be configured to display, for example, concurrently with, or on a same image with the anatomy) an indicator or image indicative of the location of the tracking sensor, and thus indicative of the location of a portion of the interventional tool (e.g., a tip of the tool) within the vessel. In some embodiments, one or more functions of at least one of the graphics processor, image processor, volume renderer, and multiplanar reformatter may be combined into an integrated image processing circuitry (the operations of which may be divided among multiple processor operating in parallel) rather than the specific functions described with reference to each of these components being performed by a discrete processing unit. Furthermore, while processing of the echo signals, e.g., for purposes of generating B-mode images or Doppler images are discussed with reference to a B-mode processor and a Doppler processor, it will be understood that the functions of these processors may be integrated into a single processor.

Figure 5:
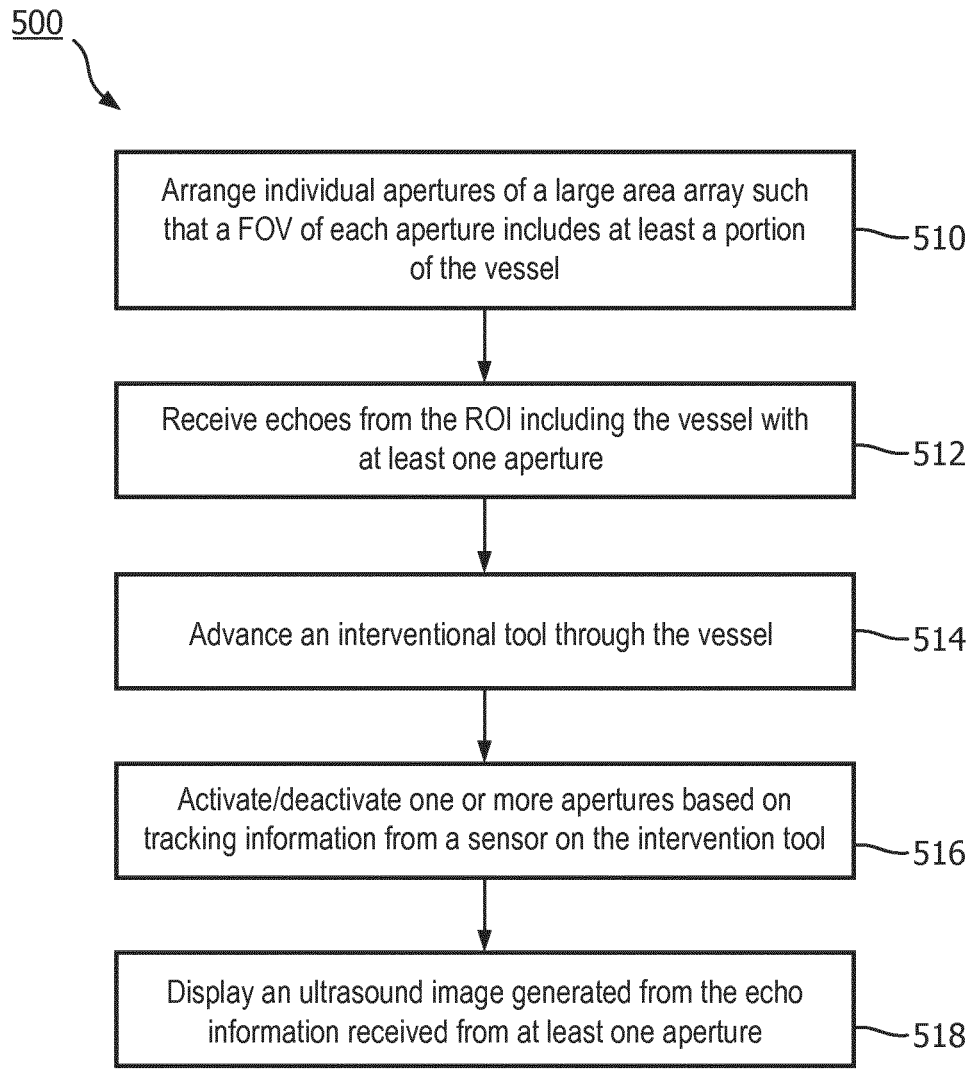
FIG. 5 is flow diagram of a process for imaging during an intervention procedure in accordance with the present disclosure.
Figure 6B:
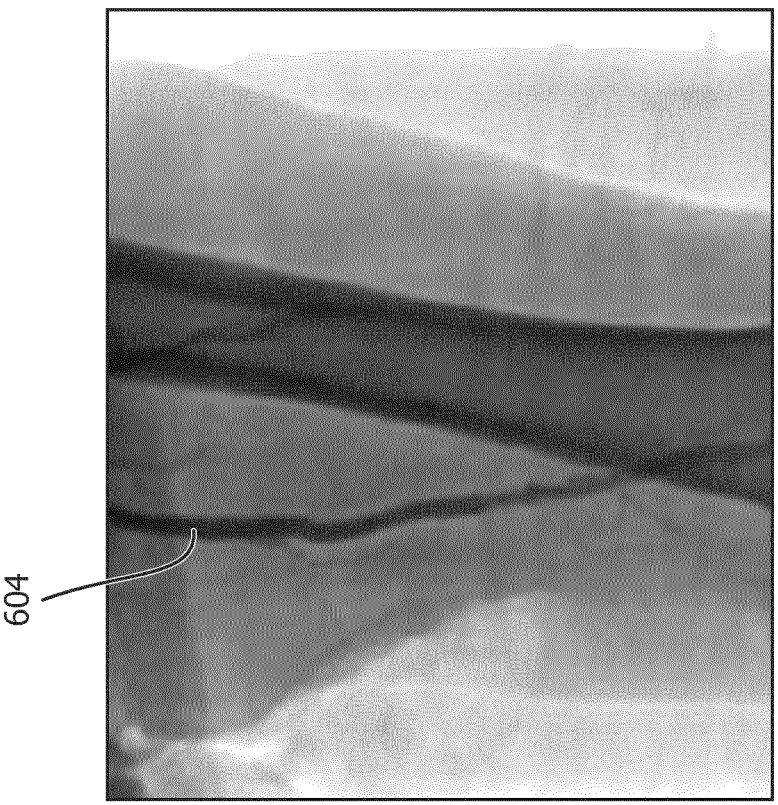
FIGS. 6A and 6B show x-ray images of a femoral artery before and after intervention.
Figure 6A:
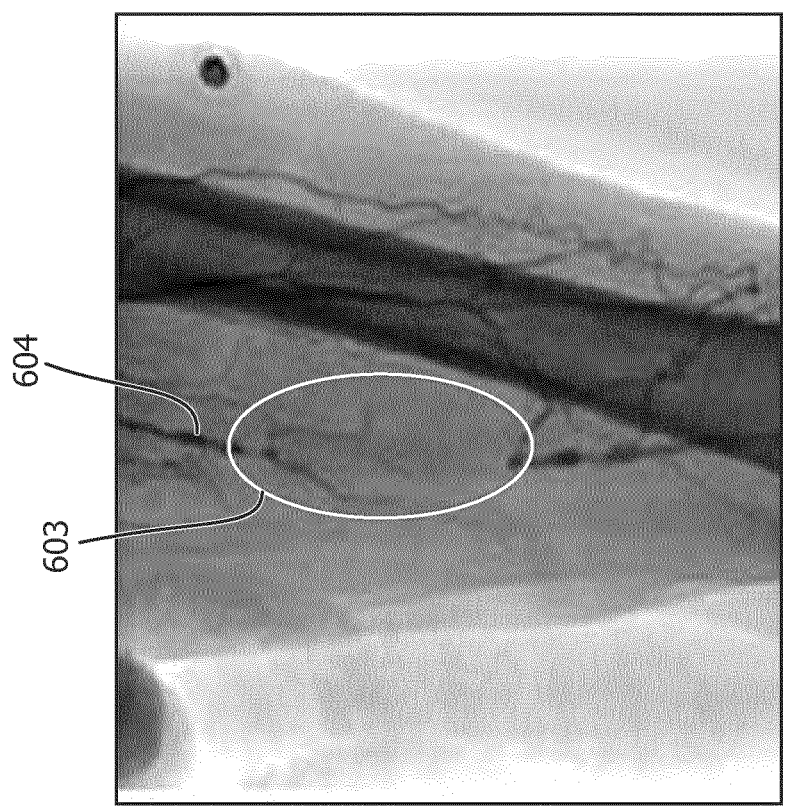

As will be appreciated, examples in accordance with the principles of this invention may provide a large field of view via an imaging modality typically adapted for much smaller fields of view (e.g., a maximum of 4 cm or in some cases up to 5 cm). The resulting field of view obtainable in accordance with the present examples may be 10 cm or greater, and in some examples up to 30 cm or greater depending on the number of individually movable patches. As described, a field of view of a large area array according to the present disclosure may be adjustable to follow the path (e.g., curvature in the path) of a vessel and/or to conform to a surface of the subject to be imaged. As described, each aperture may be independently positionable (e.g., manually by the user or electronically by the system) such that each aperture includes at least a portion of the vessel in its FOV. In examples, the individual apertures are adjusted to obtain an optimal view of the vessel (e.g., a view which transects the vessel along all or most of the length of the portion of the vessel which is in the FOV of the vessel). In one embodiment, a large area array, e.g., one including 2-6 patches, may enable imaging of an area of approximately 6×25 cm$^2$, through automatic electronic selection of the appropriate aperture to be active at any given time and without the need to physically move the array during imaging. As described, each individual aperture may be provided by a sub-array (e.g., a 1D or a 2D array) of capacitive micromachined ultrasonic transducer (CMUT) elements, piezoelectric transducer elements, or other type of ultrasonic transducer elements currently known or later developed FIG. 5 shows a block diagram of a process 500 for imaging during an intervention procedure. The process 500 may include positioning the ultrasound transducer assembly (e.g., large area array 110) with respect to a subject such that a field of view of the ultrasound transducer assembly includes a vessel of the subject, as shown in block 510. As described, the large area array may include a plurality of independently controllable apertures (e.g., a plurality of 1D or 2D sub-arrays which are independently operable to obtain ultrasound images and/or are movable in relation to one another). In some examples, the positioning may include adjusting the positions of individual ones of the apertures, which may be performed manually by the user or responsive to electronic control, such that each aperture includes at least a portion of the vessel. In some embodiments, the positional adjustments are made prior to the intervention procedure and the positions are maintained (e.g., by holding components of the frame) during the intervention procedure. In addition, images may be obtained of the vessel using the extended FOV of the larger area array prior to the intervention procedure for building a model of the vessel which may be used for further guidance during the intervention procedure. In some embodiments, further positional adjustments of individual apertures (e.g., responsive to electronic control) may be made during the intervention procedure.

As shown in block 512, the process 500 may include transmitting ultrasound with one or more apertures of the large area array (e.g., at least one active aperture) and receiving echoes with the active aperture(s). An ultrasound imaging apparatus (e.g., apparatus 120) may generate and display images based on the received echoes for visualizing an interventional tool within the vessel, as shown in block 518.

As described the system is operatively associated with a tracking system and a sensor positioned on the interventional tool. The sensor communicates tracking information to the tracking system for determining the position of the interventional tool relative to an active aperture. Thus, as the interventional tool is advance through the vessel, as shown in block 514, the process may further include receiving, by the tracking system, tracking information from the tracking sensor. The imaging system is configured to activate (i.e., communicatively couple) and/or deactivate (i.e., communicatively decouple) one or more apertures from the plurality of apertures of the large area array based on the tracking information, as shown in block 516.

During an example process, most of the apertures (e.g., in the case of single active apertures, all but one of the apertures of the array) are inactive, typically an aperture at one end of the array, which is the closest to the entry point of the interventional tool. As the tool advances in the vessel, activation of successive apertures in the direction of tool advancement, and deactivation of apertures from the opposite end, may occur automatically responsive to commands generated based on the tracking information. For example, the activation of successive apertures may be performed by a multiplexer based on the tracking information. In some examples, only a single aperture may be active at any given time and the multiplexer may couple an aperture next to the currently active aperture and decouple the currently active aperture upon a determination that the tracking sensor has left or is near the boundary of the FOV of the active aperture.

In some examples, multiple but not all apertures may be active at any given time (e.g., in the case of a high channel count ultrasound scanner), and the multiplexer may be configured to activate an aperture adjacent to one side of one or more currently active apertures and deactivate an aperture adjacent to the opposite side of the one or more currently active apertures based on the tracking information.

In some examples, the commands to selectively activate/deactivate apertures may additionally or alternatively be generated responsive to information about the location of the intervention tool which be obtained from image processing. For example, image segmentation, edge detection or other techniques may be used to determine or confirm whether the tip of the tool is within the field of view of the active aperture or where within the FOV the tip is located. If determined to be outside of or near the boundary of the FOV, the next aperture may be activated. The process (e.g., of electronically activating successive apertures as the tool is advance) is repeated until the intervention procedure (e.g., CTO crossing) is completed.

As will be appreciated, one or more benefits may be achieved by the present invention. For example, because the present disclosure proposes the use of ultrasound instead of X-Ray, which is the typical modality for imaging larger areas such as may be needed for PAD diagnosis or treatment, harmful X-Ray exposure is limited and potentially eliminated in accordance with the examples herein. The use of radiation contrast is also a disadvantage in fluoroscopic procedures, due to the risk of contrast-induced nephropathy (CIN) for patients. This invention obviates the need for using contrast. Furthermore, the present disclosure may improve the visualization of vessels including in chronic total occlusions (CTOs), where blocked arteries and thus the "pathway" for the crossing wire and catheter to take, cannot be visualized under X-Ray arteriogram. The invention may also provide additional information of depth (volumetric imaging) as well as blood flow (Doppler) as compared to 2D view of arteriogram. Current technology lacks real-time feedback for the advancement of the interventional device (guide-wire, catheter) in the occluded vessel. The present invention may also improve the workflow by minimizing the need for a skillful sonographer or radiology technicians to capture X-ray images or ultrasound panoramic view throughout the interventional procedures and post-procedure evaluation. Further improvements in the imaging and the workflow may be achieved from optional in-situ tracking of the intervention device. Furthermore, in addition to ensuring the tracking sensor is within the active imaging window, the selective activation/deactivation of apertures of the array may save energy and reduce the processing throughput of the ultrasound system. It will be understood that the embodiments herein need not provide some or any of these benefits.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
an ultrasound transducer assembly comprising a plurality of apertures that are configured to transmit signals toward and receive signals from a region of interest (ROI) of a subject, wherein a position of the ultrasound transducer assembly is maintained with respect to the ROI;
a tracking sensor disposed within the subject and configured to move within the ROI, the tracking sensor being responsive to signals transmitted by the apertures;
at least one processor in communication with the ultrasound transducer assembly and the tracking sensor, wherein the processor is configured to:
generate a first image of a first portion of the ROI from signals received from a first aperture of the plurality of apertures; and
identify a position of the tracking sensor using tracking data from the tracking sensor that is generated in response to at least one signal transmitted by the first aperture; and
a multiplexer that is in communication with the at least one processor and the ultrasound transducer assembly, wherein the multiplexer is configured to:
selectively control the plurality of apertures based on the identified position of the tracking sensor;
activate, in response to the identified position, at least one aperture of the plurality of apertures to transmit signals toward the ROI; and
deactivate, in response to the identified position, at least one other aperture of the plurality of apertures from transmitting signals toward the ROI; and
wherein the processor is further configured to generate a second image of a second portion of the ROI from signals received from a second aperture of the plurality of apertures, wherein the second aperture of the plurality of apertures is activated by the multiplexer based on the identified position of the tracking sensor, wherein the second portion of the ROI is different from the first portion of the ROI.

2. The system of claim 1, wherein the first and second portions of the ROI are overlapping or non-overlapping.

3. The system of claim 2, wherein the multiplexer is configured to communicatively couple only a single aperture to an ultrasound imaging apparatus at any given time, and wherein the multiplexer is configured to communicatively couple an aperture adjacent to a currently active aperture and to decouple the currently active aperture responsive to receipt of an indication of the tracking sensor approaching a boundary of or exiting the FOV of the currently active aperture.

4. The system of claim 1, wherein the multiplexer is configured to couple input signals associated with an aperture adjacent to a first side of a currently active aperture responsive to receipt of an indication of the tracking sensor approaching a boundary of or exiting the FOV of the currently active aperture.

5. The system of claim 4, wherein the multiplexer is further configured to decouple input signals associated with an aperture adjacent to a second side opposite the first side of the currently active aperture responsive to receipt of the indication.

6. The system of claim 1, wherein the tracking sensor comprises an ultrasound receiver, and wherein the at least one processor is configured to determine a location of the receiver with respect to an active aperture.

7. The system of claim 1, wherein the ultrasound transducer assembly comprises a frame configured to enable each of the plurality of apertures to be moved relative to one another to position the plurality of apertures such that a field of view (FOV) of each of the plurality of apertures includes a portion of a vessel.

8. The system of claim 7, wherein a combined FOV of the ultrasound transducer assembly has a length of 10 cm or greater.

9. The system of claim 8, wherein the combined FOV of the ultrasound transducer assembly has a length of 30 cm or greater.

10. The system of claim 7, wherein the ultrasound transducer assembly comprises a multi-patch array including a plurality of patches, and wherein the frame is configured to enable each of the plurality of patches to slide relative to one another.

11. The system of claim 1, wherein the ultrasound transducer assembly comprises a plurality of ultrasound probes and wherein an array of each of the plurality of ultrasound probes provides respective one of the plurality of independently controllable apertures.

12. The system of claim 3, wherein respective arrays of two adjacent apertures are spaced by a gap, and wherein the ultrasound imaging apparatus comprises a transmit controller configured to steer beams of the respective arrays to image an intermediate region of the subject associated with the gap.

13. The system of claim 1, wherein the at least one processor is configured to perform image segmentation, edge detection, contrast enhancement, or a combination thereof, and wherein activation of apertures is further based on the image segmentation, edge detection, contrast enhancement, or the combination thereof.

14. A method of ultrasound imaging during an intervention procedure, comprising:
transmitting, using an ultrasound transducer assembly, ultrasound toward a region of interest (ROI) of a subject, the ROI including a vessel, wherein the ultrasound transducer assembly comprises a plurality of independently controllable apertures, and wherein the transmitting includes transmitting ultrasound with a first aperture of the plurality of independently controllable apertures;
maintaining a position of the ultrasound transducer assembly with respect to the ROI;
receiving echoes with the first aperture of the plurality of independently controllable apertures;
receiving, by at least one processor operatively associated with the ultrasound transducer assembly, tracking information from a tracking sensor positioned on an interventional tool in the vessel;
activating a second aperture of the plurality of independently controllable apertures based, on the tracking information, wherein the activating the second aperture of the plurality of independently controllable apertures includes receiving the tracking information by a multiplexer connecting each of the independently controllable apertures to the at least one processor, and communicatively coupling the second aperture of the plurality of independently controllable apertures to the at least one processor based on the tracking information;
deactivating at least one aperture of the plurality of independently controllable apertures different from the second aperture based on the tracking information; and
generating and displaying, responsive to the echoes, an ultrasound image of the ROI including the vessel.

15. The method of claim 14, wherein each of the independently controllable apertures is movable relative to one another, the method further comprising adjusting a position of individual ones of the plurality of independently controllable apertures such that a field of view of each of the plurality of independently controllable apertures includes a portion of the vessel.

16. The method of claim 14, wherein the ultrasound transducer assembly comprises a plurality of ultrasound probes, and wherein the positioning the ultrasound transducer assembly includes moving one or more of the plurality of ultrasound probes such that respective arrays of the one or more of the plurality of ultrasound probes are arranged to image at least a portion of the vessel.

17. The method of claim 14, wherein the ultrasound transducer assembly comprises a multi-patch transducer array, and wherein the positioning the ultrasound transducer assembly includes moving one or more patches of the multi-patch array relative to other patches of the multi-patch array.

18. The method of claim 14, further comprising decoupling, by the multiplexer, a currently active aperture from the at least one processor when another one of the plurality of independently controllable apertures is activated.

19. The method of claim 14, wherein the second aperture activated comprises an aperture adjacent to one side of one or more currently active apertures and the at least one aperture deactivated comprises an aperture adjacent to the opposite side of the one or more currently active apertures.

20. The method of claim 14, further comprising imaging the vessel prior to advancing the interventional tool through the vessel to determine a target position for each of the plurality of apertures in which the respective apertures includes a portion of the vessel, and wherein the target position is maintained during the advancing of the interventional tool through the vessel.

21. A non-transitory computer-readable medium comprising executable instructions, which when executed cause a processor of medical imaging system to perform any of the methods of claim 14.

22. An ultrasound imaging system comprising:
an ultrasound transducer assembly comprising a plurality of independently controllable apertures, wherein each of the independently controllable apertures is configured to transmit signals to and receive signals from a region of interest (ROI) of a subject, the ROI having a length from about 10 cm or greater, wherein a position of the ultrasound transducer assembly is maintained with respect to the ROI;
an ultrasound imaging apparatus coupled to each of the plurality of independently controllable apertures and configured to generate ultrasound images based on the received signals;
a tracking sensor operatively associated with a tracking system and configured to be positioned on an interventional tool during an intervention procedure; and
a multiplexer connecting each of the independently controllable apertures to the ultrasound imaging apparatus, wherein the multiplexer is configured to communicatively couple one or more of the plurality of independently controllable apertures to the ultrasound imaging apparatus based on tracking information received from the tracking system and activate at least one aperture of the plurality of independently controllable apertures and deactivate at least one other aperture of the plurality of independently controllable apertures, in response to the tracking information.

23. The system of claim 22, wherein the ROI has a length of less than 50 cm.

24. The system of claim 22, wherein the length of the ROI is based on a number of the independently controllable apertures currently activated.

* * * * *